United States Patent [19]

Cyrulnik

[11] Patent Number: 5,044,006
[45] Date of Patent: Aug. 27, 1991

[54] MICROWAVE FREQUENCY MODULATION OF X-RAY BEAM FOR RADIO THERAPY TREATMENT SYSTEM

[76] Inventor: Reuven A. Cyrulnik, 639 Marshall St., Long Beach, Calif. 90807

[21] Appl. No.: 515,192

[22] Filed: Apr. 27, 1990

[51] Int. Cl.$^5$ .......................... G21K 1/00; G21K 5/00; A61N 5/02
[52] U.S. Cl. ........................................ 378/145; 600/2; 378/64; 378/65; 378/113; 378/138
[58] Field of Search ................... 378/64, 65, 113, 138, 378/145; 128/422, 364, 736, 664, 665; 600/1, 2

[56] References Cited

U.S. PATENT DOCUMENTS

| | | | |
|---|---|---|---|
| 4,172,979 | 10/1979 | Morrison | 378/65 |
| 4,307,726 | 12/1981 | Paulson et al. | 128/653 |
| 4,515,165 | 5/1985 | Carroll | 128/664 |
| 4,557,272 | 12/1985 | Carr | 128/736 |
| 4,726,046 | 2/1988 | Nunan | 378/65 |
| 4,815,447 | 3/1989 | Mills | 600/1 |
| 4,815,448 | 3/1989 | Mills | 600/2 |

Primary Examiner—Edward P. Westin
Assistant Examiner—Kim-Kwok
Attorney, Agent, or Firm—Helfgott & Karas

[57] ABSTRACT

Radiation of specific material within a subject is accomplished by use of a beam of x-radiation modulated at a microwave frequency. The beam with its modulation is directed at the subject wherein the material interacts with the beam to extract a portion of the radiant energy carried by the beam. In the interaction, an electric field at the modulating frequency appears at the material. By selecting the modulated frequency equal to a resonant interactive microwave frequency of the material, a photon at the microwave frequency is absorbed by the material to alter its physical and chemical properties. By way of example, the material may be an oncogene or virus having a macromolecule and constituting a malignancy within a living subject. Absorption of the modulated radiation selectively destroys the malignancy. The klystron is disposed along the path of an electron beam in an x-ray source for modulating the electron beam and the resulting x-ray beam. An array of x-ray sources and detectors is arranged symmetrically about a site of the subject. Sequential activation of the x-ray sources along with a scanning of the microwave modulating frequency permits measurement of absorption of radiant energy at the various modulation frequencies. This information is used to select the appropriate modulation frequency.

14 Claims, 3 Drawing Sheets

MICROWAVE FREQUENCY MODULATION OF X-RAY BEAM FOR RADIO THERAPY TREATMENT SYSTEM

BACKGROUND OF THE INVENTION

This invention relates to the application of x-radiation to a subject and, more particularly, to a modulation of an x-ray beam with a microwave signal to produce in the subject radiation at a microwave frequency to be absorbed by pathological material including macromolecules, such as oncogenes, for treatment of malignancy.

Microwave radiation and x-rays have each been employed in medical procedures for destroying malignant material, particularly body tissue afflicted with various forms of cancer. Energy of the radiation is absorbed by the material with a resultant change in the physical and the chemical properties of the material, this resulting in a termination of the malignancy. The biological material to be treated by the radiation may be formed of desoxyribonucleic acid, the genetic material of which the chromosomes of human cells are composed. The desoxyribonucleic acid consists of pairs of macromolecules containing a backbone of units of five carbon atoms linked by phosphorous and oxygen atoms, each unit having a side chain of a purine or pyramidine base. Viruses and genes that cause cancer (oncogenes) consist of such macromolecules, and have lengths on the order of 4,000 or more bases, or a backbone of some 20,000 atoms.

In order to understand the interaction of the microwave radiation with the macromolecules, it is useful to consider some basic concepts in the energy levels of electrons of the various atoms arranged in the macromolecules. In accordance with electrostatic theory, the potential energy of an electron is inversely proportional to the distance of the electron from the nucleus of the atom, the distance defining an equipotential surface. The electric field, or attractive force between the nucleus and the electron, is given by the gradient of the potential surface and, accordingly, varies with the inverse square of the distance. A transfer of an electron from one of the allowable quantum energy levels to a second energy level is accomplished by the expenditure or absorption of an amount of energy equal to the difference of potential between the two levels. In terms of mathematics, apart from a proportionality constant, the energy values of the two levels are given by $(1/a)$ and $(1/b)$ wherein a and b are the distances between the nucleus and the energy level. This is a simplistic model assuming spherical energy levels. During a transition of energy state, wherein an electron moves from one potential level to the other potential level, the change in energy is proportional to $(1/a - 1/b)$ which is equal to $(b-a)/ab$. This being equal to $d/ab$ wherein d is the difference between a and b, and is understood to be very much smaller than either a or b. Therefore, the energy expended in a transition of electrons between two potential levels is proportional to the distance between the two potential levels. The amount of energy to totally remove an electron from an atom is equal to the energy of the potential level, which, as noted above, is inversely proportional to the radius of the potential surface.

Interaction of a beam of radiation with molecules of material is characterized by a transfer of energy from the beam to an electron in an atom of a molecule. The energy in a photon of the beam is proportional to the frequency of the radiation, the proportionality factor being the Plank constant. In the situation wherein the energy of the photon is equal to the transition energy required to elevate an electron from an inner energy level to an outer energy level, the transfer of energy occurs readily with extinction of the photon. In this situation, the frequency of the radiation has a value, which may be referred to as the resonant frequency, which provides the photon with the requisite energy for accomplishing the transition in electron energy state.

The foregoing analysis has been based on a simplistic model in which each of the atoms of the molecule is provided with spherically shaped electron energy levels. In actuality, the electron energy levels among the thousands of atoms in macromolecules, at least in the outer energy levels, are altered both in physical shape and in energy level. This results in numerous energy levels which characterize the specific macromolecule and the material composed of the macromolecules. The lowest energy transitions for electrons in single atoms result in absorption of radiation in the spectrum of visible light, this radiation having a frequency of approximately $2 \times 10 \exp(14)$ Hertz (Hz). The frequency of radiation for absorption at the lowest transition energy of molecular energy levels varies inversely with the size of the molecule. A molecule of 20,000 atoms in length would be expected to absorb radiation at a frequency of approximately 1/20,000 that of light, namely, a frequency of $10 \exp(10)$ Hz, this being in the microwave range and having a wavelength of three centimeters.

A problem exists with presently available equipment and methodology for the administration of microwave radiation to subject matter, for removing a malignancy by way of example, in that the microwave radiation has minimal penetration. X-ray, on the other hand, is transmitted throughout the subject relatively non-selectively, rather than being directed to specific regions of interest. The specific regions embedded within the subject require the radiation therapy while the remaining portion of the subject does not require such therapy. While it may be possible to illuminate the subject from different directions so as to concentrate the dosage at limited absorption, the specific regions, relatively large doses are required because of limited absorption, and a significant amount of radiation is absorbed by the remainder of the subject. This reduces the radiation available for the specific regions, and may interfere with the functioning of the remaining portion of the subject.

SUMMARY OF THE INVENTION

The aforementioned problem is overcome and other advantages are provided by an apparatus and methodology of the invention which provides for the generation of the radiation by use of an x-ray beam modulated in amplitude at a microwave frequency. The x-ray beam readily penetrates biological subject matter, such as a persons head, to deliver radiant energy to a specific site, such as the site of a tumor. The material of the tumor interacts with the x-ray beam to detect a portion of the energy of the beam. Such a detection process is a non-linear process which regenerates the microwave signal at the site of the tumor. The regenerated signal is an electromagnetic microwave signal having photon energy suitable for interaction with the electrons of the macromolecules of the tumor, thereby to destroy the tumor.

It is an object of the invention to modulate an x-ray beam at a frequency suitable for the application of a microwave signal at a specific site or sites within a subject. It is a further object of the invention to scan the subject to determine which microwave frequency or frequencies would be beneficial.

The invention can be practiced by use of a computerized-tomographic (CT) scanner, also referred to as a CAT (computer aided or axial tomography) scanner, in which individual ones of the x-ray sources are modified to include a device for modulating the beam. Preferably, the modulation alters the amplitude of the x-ray beam, such as by turning the beam on and off. In a preferred embodiment of the invention, the modulating device comprises a klystron disposed about the path of the electron beam which illuminates the target of the source to generate the x-ray beam. By energizing the klystron with a microwave signal, intense electric fields are developed within cavities of the klystron, the intense electric fields tending to bunch the electrons together in a sequence of electron pulses which illuminate the target at a repetition frequency equal to the frequency of the microwave signal. The actual pulses may have a waveform which can be characterized as sinusoidal or square depending on the nature of the bunching of the electrons; however, the basic fundamental frequency component of the train of electron pulses is equal to the frequency of the microwave signal. The resulting x-ray beam appears as a train of pulses of x-radiation at the same frequency as the microwave modulation frequency. The microwave frequency is selected to equal the resonant frequency for interaction with the selected material of the subject.

In order to scan the subject to determine the value of the resonant frequency or resonant frequencies, the frequency of the microwave modulating signal is varied, or swept, by a series of small steps during the duration of the x-ray beam to provide a swept-frequency modulation of the beam. The CT scanner includes detectors which output signals signifying the intensity of x-radiation which propagates through the subject to impinge upon the detector. As is well known in the use of CT scanners, the variations of intensity, as signified by an array of detectors, are employed by computerized focusing programs to produce a synthetic image of the subject. The image is based on data obtained from beams propagating through the subject at differing angles of orientation.

In accordance with the invention, the data outputted by the detectors is examined as a function of time to note reductions in the intensity of a received beam of x-radiation. A reduction in intensity signifies the absorption of energy of the beam by photon interaction with the subject. Since the modulating frequency is being swept at a predetermined rate, the time of occurrence of an absorption of radiation is indicative of the value of the modulating frequency which produces the absorption. By addressing a memory in synchronism with the stepwise sweeping of the modulation frequency, the memory records the value or values of resonant frequency at which interaction occurs. An operator of the CT scanner then employs this information to select the microwave modulating frequency at a proper value for radiating the subject.

BRIEF DESCRIPTION OF THE DRAWING

The aforementioned aspects and other features of the invention are explained in the following description, taken in connection with the accompanying drawing wherein.

DETAILED DESCRIPTION

Figure 1:
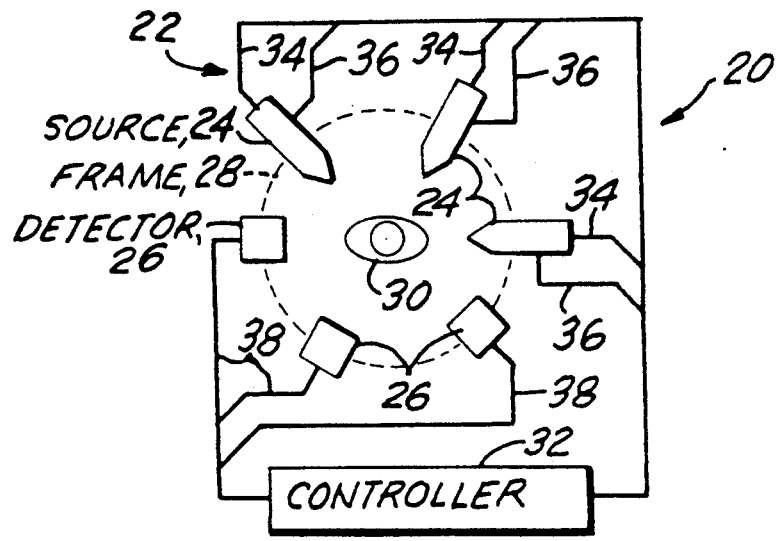
FIG. 1 is a diagrammatic view of a CT scanner modified for the practice of the invention.

FIG. 1 shows a radiating system 20 including a CT scanner 22 which has been modified, as will be described below, to enable practice of the invention. The scanner 22 includes a plurality of x-ray sources 24, of which three are shown by way of example, and a plurality of x-ray detectors 26, of which three are shown by way of example. The sources 24 and the detectors 26 are held in their respective positions by a frame 28 which encircles a subject 30 which is typically a living creature such as a human being or an animal. The sources 24 and the detectors 26 are positioned symmetrically about the subject 30, and are connected electrically to a controller 32 which includes circuitry for the practice of the invention as will be described below. In particular, it is noted that each of the sources 24 is connected by two electric lines to the controller 32, a first of the lines 34 providing an electric signal which activates the source 24, and a second of the electric lines 36 providing an electric signal which modulates the x-ray beam at a predetermined modulation frequency. The detectors 26 are connected by electric lines 38 to the controller 32 for inputting data about detected radiation to the controller 32.

Figure 2:
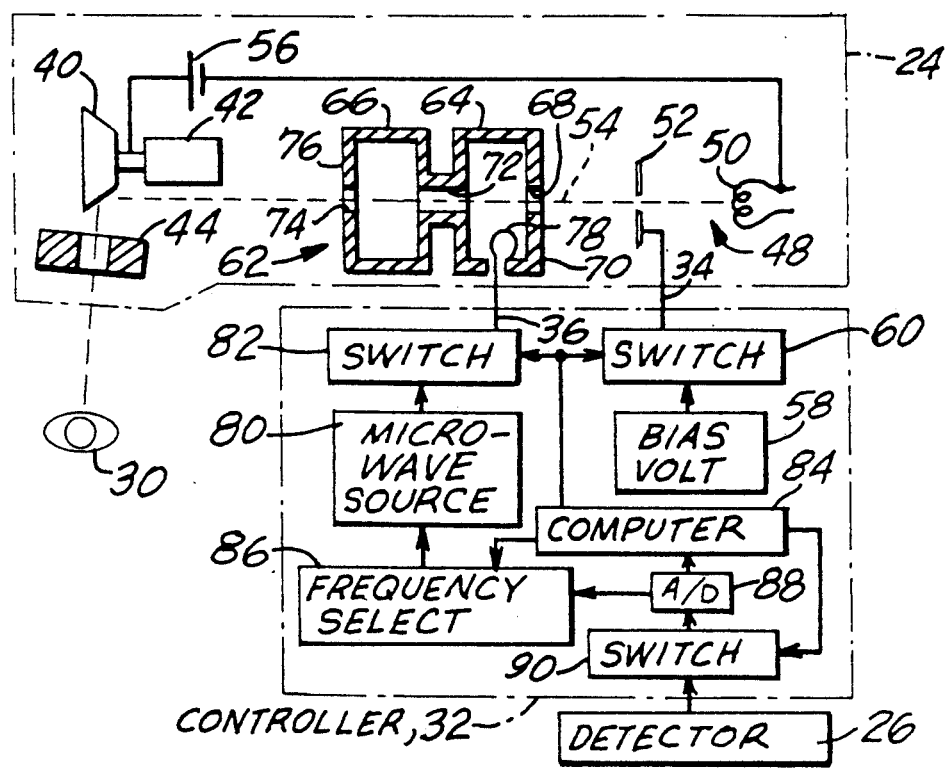
FIG. 2 is a diagrammatic view of an x-ray source employed in FIG. 1, the apparatus of FIG. 2 providing for modulation of an x-ray beam.

FIG. 2 shows details in the construction of one of the sources 24, as well as components of the controller 32, and an interconnection between the controller 32 and one of the detectors 26. All of the sources 24 function in the same manner, and all of the detectors 26 function in the same manner. The x-ray source 24 comprises a target 40 rotated by a motor 42, and a collimator 44. The collimator is positioned along a path of x-rays emanating from the target 40 for defining an x-ray beam 46 directed towards the subject 30. The source 24 further comprises an electron gun 48 which includes a filament 50 and an electrode assembly 52. The filament 50 is used to emit electrons which are accelerated by electric potentials on the electrode assembly 52 and the target 40 relative to the filament 50, the accelerated electrons forming a beam 54. Electrons of the beam 54 strike the target 40 to generate the x-rays, the process of generation of the x-rays being well-known. A battery 56 connected between the target 40 and the filament 50 symbolically illustrates electric potential in the range of thousands of volts applied between the target 40 and the filaments 50. Electric potential for the electrode assembly 52 is provided from a bias voltage source 58 within the controller 32, the voltage of the source 58 being coupled to the electrode assembly 52 via a switch 60 also located within the controller 32.

In accordance with a feature of the invention, the x-ray source 24 further comprises a klystron 62 of which two cavities 64 and 66 are shown in longitudinal sectional view, the cavity 64 being located between the cavity 66 and the electrode assembly 52. The central axis of the klystron 62 coincides with an axis of the electron beam 54. The beam 54 passes through an aperture 68 in an end wall 70 of the cavity 64, a tubular region 72 interconnecting the cavities 64 and 66, and an aperture 74 in an end wall 76 of the cavity 66. A probe 78 in the form of a loop is located in the cavity 64 for receiving inputted microwave power. Microwave power is provided by way of a microwave signal generated within a microwave source 80 located within the controller 32, the microwave signal being coupled from the source 80 to the probe 78 via a switch 82 also located within the controller 32.

Also included within the controller 32 is a computer 84, a frequency selector 86, an analog-to-digital converter 88 and a switch 90. Signals from a detector 26 are coupled by the switch 90 to the converter 88, the converter 88 converting the analog signals of the detector to digitally formatted signals to be inputted to the computer 84.

Figure 3:
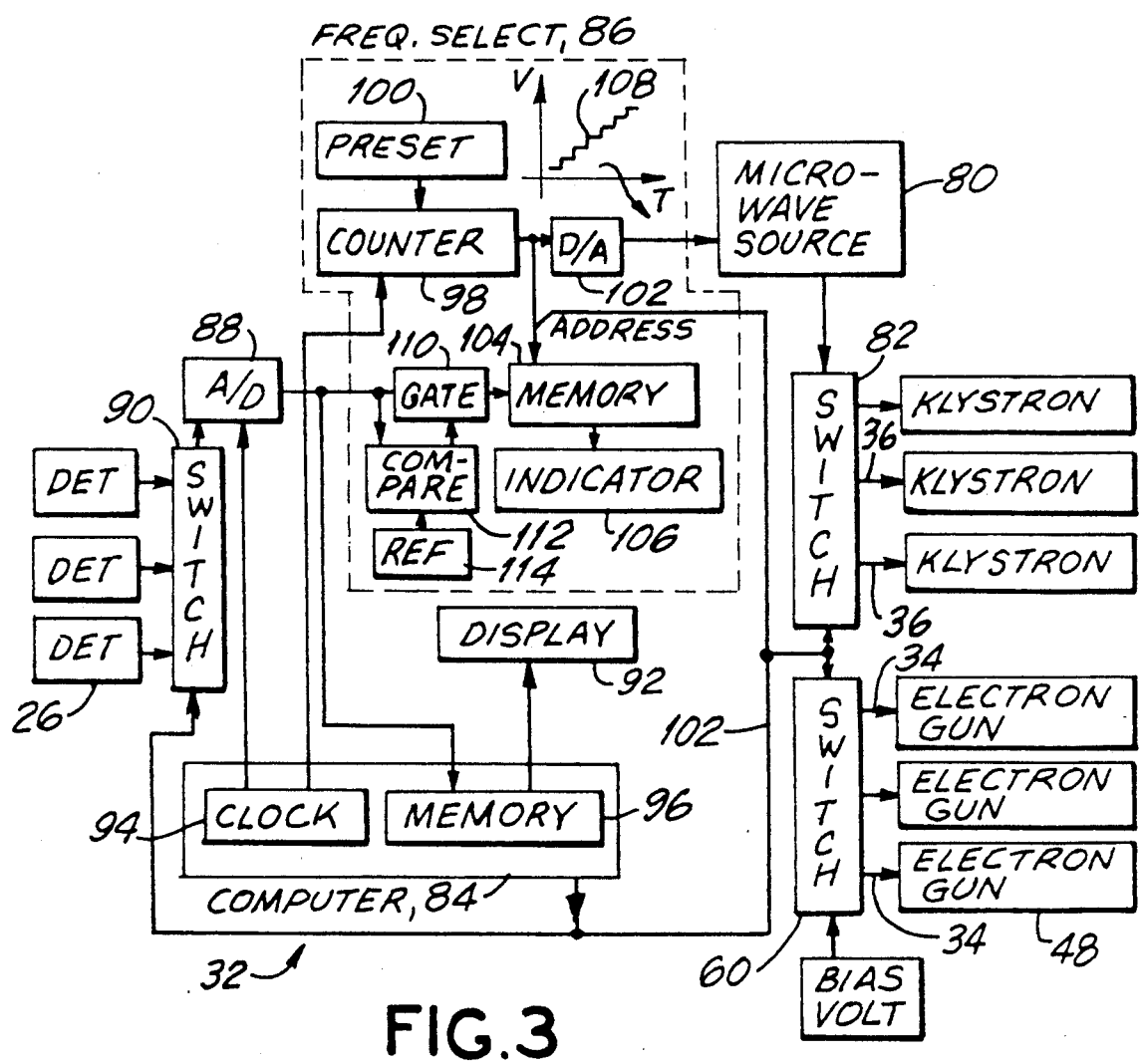
FIG. 3 shows electrical circuitry of a controller of FIG. 1 employed in practicing the invention.

FIG. 3 shows further details in the interconnection of the controller 32 with the detectors 26, and with the klystron 62 and the electron gun 48 in respective ones of the x-ray sources 24. FIG. 3 also shows further details in the construction of the controller 32, including components of the frequency selector 86. The controller 32 includes a display 92 upon which the computer 84 outputs a synthesized image of the subject 30 when the scanner 22 is operating in a normal computerized tomographic mode of x-ray imaging. Included within the computer 84 are a clock 94 and a memory 96 which are employed both in normal computerized tomographic imaging and in the use of the CT scanner 22 for operating with modulated x-ray beams. In the case of normal CT imaging, the memory 96 stores x-ray data obtained from the detectors 26, as well as a program for combining the data to produced the synthesized image.

The frequency selector 86 comprises a counter 98, a preset element 100, a digital-to-analog converter 102, a memory 104, and an indicator 106. The frequency selector 86 is operative in either of two modes, namely, a frequency sweeping mode and a preset frequency mode for the modulation of the x-ray beam.

In the operation of the frequency selector 86 in the frequency sweeping mode, the computer 84 transmits clock pulses from the clock 94 to the counter 98. The counter 98 proceeds to count up, and applies the output count to the converter 102 for converting the count into an analog voltage proportional to the value of the count. As the count increases linearly in time, the analog voltage outputted by the converter 102 increases stepwise in the form of a stepwise ramp 108, indicated in a graph appended alongside the converter 102. In the graph portraying the ramp 108, the vertical axis represents volts, and the horizontal axis represents time. The stepwise ramp voltage 108 is applied by the converter 102 to a frequency control terminal of the microwave source 80. By way of example in the construction of the microwave source 80, it is noted that the source 80 includes a well-known oscillator circuit (not shown) which may include one or more diodes having reactance dependent on applied voltage. By varying the voltage at the input frequency control terminal, the frequency of oscillation is varied so that the input voltage effectively controls the oscillation frequency of the source 80.

During application of the stepwise ramp voltage 108 to the microwave source 80, the duration of each step of the voltage waveform is sufficiently long to allow the klystron 62 of a source 24 to attain equilibrium at the commanded frequency, and to allow sufficient time for one of the detectors 26 to detect radiation and transmit data to the computer 84. The output count of the counter 98 is also applied as an address to the memory 104 to enable the memory 104 to store data received by a detector 26 with respect to the absorption of radiant energy of the modulated x-ray beam by macromolecules. For this purpose, the frequency selector 86 further comprises a gate 110, a comparator 112, and a source 114 of reference voltage.

During the frequency sweeping mode, signals outputted by a detector 26 in response to incident radiation are coupled via the switch 90 to the converter 88 to be outputted as a digital signal representing the intensity of the incident radiation. The comparator 112 compares the output signal voltage of the converter 88 with a reference voltage of the source 114 to determine that the signal represents a significant absorption of radiant energy by macromolecules. In the event that absorption is indicated, the comparator 112 opens the gate 110 to allow the signal to pass from the converter 88 into the memory 104. Thereby, the memory 104 stores significant signals at an address corresponding to the step of the voltage ramp 108 and corresponding to the value of modulation frequency for which significant absorption of radiant energy has been observed. Values of x-ray beam intensity of each value of resonant frequency at which absorption has been observed are outputted by the memory 104 to the indicator 106 for presentation to personnel operating the radiating system 20. Thereby, during the swept frequency mode of operation, the frequency selector 86 provides for a succession of test values of frequency of the microwave modulation, and presents a record of those frequencies for which there has been absorption of radiant energy by macromolecules.

After selection of a suitable resonant frequency, there follows operation of the frequency selector 86 in the preset frequency mode wherein the modulation of the x-ray beam is accomplished at a single predetermined frequency. In the preset frequency mode, the computer 84 discontinues the application of the clock pulses from the clock 94 to the counter 98, and the counter 98 is preset manually, by operating personnel, to the count representing a desired resonant frequency. The presetting is accomplished by use of the preset element 100 which may be any one of a number of well-known digital input devices, such as a keyboard or set of wheels by which a digital number is manually inputted. Thus, the counter 98 outputs a fixed count designating the single resonant frequency for which modulation of the x-ray beam is desired. By modulation of the x-ray beam at the fixed resonant frequency, energy is transferred from the beam to specific macromolecules, such as the macromolecules of a tumor, in the subject 30 for destruction of the tumor.

Figure 4:
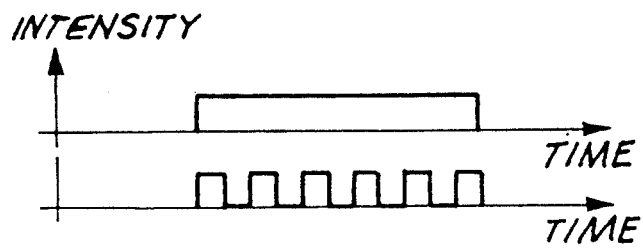
FIG. 4 is a timing diagram showing, in stylized form, an x-ray beam in unmodulated form and in modulated form.

FIG. 4 shows a set of two graphs, each representing intensity of the x-ray beam 46 (FIG. 2) as a function of time. The upper graph shows the beam in the absence of the microwave modulation. The lower graph shows the effect of the microwave modulation in producing a succession of pulses of the x-radiation. It is to be understood that these graphs are stylized by showing a square wave of approximately 50% duty cycle in the pulse train of the x-radiation. The actual duty cycle, and the shape of the pulses is dependent on characteristics of the x-ray source 24, and may vary somewhat from the idealized presentation shown in FIG. 4.

Figure 5:
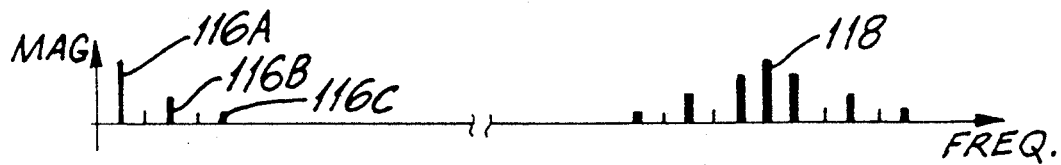
FIG. 5 is a spectral diagram showing frequency components of a square wave modulating signal and of the modulated x-ray beam.

FIG. 5 shows the corresponding frequency spectrum. Towards the left side of the spectrum, this being the lower frequency or base band spectrum, the graph shows the spectral lines of a square wave pulse-train having a repetition frequency equal to the modulation frequency. Three frequency components 116A, 116B, and 116C are shown, these components occurring at odd harmonics of the fundamental frequency 116A. To the right side of the graph is shown the spectrum of the x radiation modulated by the square wave, the x-radiation serving as a carrier for the modulation. The spectral line of the x-radiation is indicated at 118. At both the upper and the lower frequency sides of the spectral line 118 are sets of spectral lines corresponding to the modulation frequency components 116A-C. Thus, the effect of the modulation is to shift the modulation spectrum to the frequency band of the x-radiation. Therefore, the spectral components of the modulation propagate through material of the subject 30 in the same fashion as does the spectral line 118 of the x-radiation. However, upon an interaction of the x-radiation with matter containing macromolecules which have a resonant interaction frequency equal to that of the spectral line 116A, a nonlinear interaction takes place in which there is detection of at least a portion of the power of the x-ray beam, much in the manner in which a radar signal is detected by a diode detector in a radar receiver. As is well known in the operation of a radar receiver, upon detection of a radar signal, there is recovery of the modulation signal from the carrier. In the same fashion, herein in the case of the macromolecules, the microwave signal is recovered at the macromolecules with the result that the electromagnetic field of the microwave signal is impressed upon the macromolecules. This is particularly noticeable when the modulation frequency is equal to the resonant interaction frequency of the macromolecules, in which case there is a transfer of photon energy from the microwave signal to an electron of the macromolecules. This results in absorption of the x-ray, so modulated, which so alters the properties of the macromolecules, that in the case of a tumor, oncogene, virus or other malignancy, the malignancy is destroyed without damage to surrounding tissue.

With respect to the operation of the scanner 22 in a normal computerized tomographic mode, this is accomplished by turning off the microwave source 80 to terminate the modulation. Thereupon, the computer 84, by operation of the switches 60 and 90, successively activates the electron guns 48 of successive ones of the x-ray sources 24 (FIG. 1), and provides for coupling of the corresponding sequence of detectors 26 via the converter 88 to the memory 96 (FIG. 3). Thus, images are generated for each of a succession of directions of x-ray beam, which images are combined by the computer 84 to provide the synthesized image of subject matter lying in the plane of the frame 28. Each of the detectors 26 may be constructed in well-known fashion wherein an array of scintillation crystals are employed to produce imaging data.

To provide for the swept frequency mode, the foregoing procedure is altered by activating the microwave source 80 and by operating the switch 82 in conjunction with the switch 60. In addition, as described hereinabove, pulses from the clock 94 are transmitted to the counter 98. Thus, during each orientation of an x-ray beam provided by the successive sources 24 of the scanner 22 (FIG. 1), data of the absorption spectrum is attained. Output line 120 of the computer 84, which line provides a beam selection signal for controlling the switches 60, 82, and 90, is also applied as a portion of the address to the memory 104 to correlate absorption spectrum data with the respective orientations of the x-ray beam. This data can be input to the computer 84 operating in a normal computerized tomographic mode to generate a scan at each resonant frequency so as to determine, by visual inspection of the image, which frequencies are specifically and selectively absorbed by the targer (tumor) and no other structure.

Figure 6:
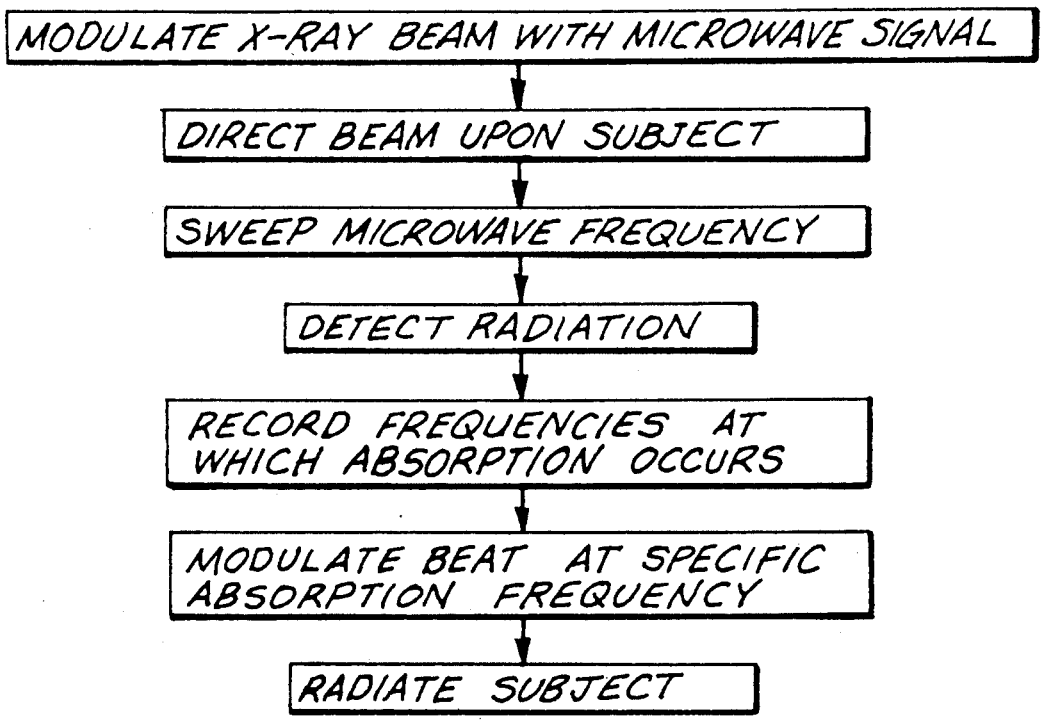
FIG. 6 is a flow chart showing a process of practicing the invention.

The procedure in the practice of the invention is shown in the flow chart of the FIG. 6. The procedure begins with a modulation of the x-ray beam with the microwave signal. The beam is directed upon the subject and the microwave modulating signal is swept in frequency. The radiation propagating from the x-ray source and through the subject is detected. This is followed by a recording of the frequencies at which absorption of radiant energy occurs. After this information has been obtained, the x-ray beam is modulated at a specific frequency for which absorption has been noted. Then, the beam while modulated at the specific absorption, or resonant, frequency is directed at the subject for radiating the subject. Photon energy is transferred to macromolecules within the subject for destruction of the macromolecules. Where the macromolecules represent a malignancy, the procedure of the invention destroys the malignancy without damaging neighboring tissue.

The invention allows one to determine when absorption is occurring, and by which structures, such as oncogene, tumor, or virus, without having to destroy empirically tissue by trial and error. The CT scanner 22 detects the absorption of a standard low radiation level, as employed in a diagnostic x-ray beam, at any point inside the body of the subject 30. The total dosage of radiation is divided among various viewing angles. By following this procedure over the spectrum of frequencies of possible absorption via oncogenes, at those frequencies which are absorbed by the genetic material unique to the tumor or malignancy, that tumor material and only that tumor material will appear as absorbent on the scan.

The spectrum of microwave frequencies, as noted above, can be impressed on the x-ray beam as each of a plurality of angles during the course of a single scan by systematically varying the modulation frequency. The klystron 62 operates at the modulation frequency. Since absorption occurs in $10 \exp(1-10)$ seconds, an x-ray beam which has a frequency of $10 \exp(17)$ Hz can accommodate $10 \exp(7)$ different microwave frequencies of modulation. Thus, each of the approximately 1,000 human genes could be tested for unique absorption at up to 10,000 frequencies. As explained above with reference to the frequency selector 86 of FIG. 3, during the generation of the frequency scan, the converter 88 is operated by the clock 94 to sample a detector output at specific increments of delay after initiation of the scan. The time delay is counted out by the counter 98 in correspondence with the values of frequency so that each absorbing structure, such as a tumor, is sensed by a detector 26 when the resonant frequency is selected.

Although only a small portion of the energy of the x-ray beam is utilized at any given modulating frequency, this is sufficient to produce the same amount of absorbed energy as occurs in an ordinary CAT scan. In an ordinary plane skull x-ray series (which contains the same amount of radiation to which the patient is exposed in a CT scan), approximately 3% of the x-ray beam is absorbed in total, of which the brain absorbs 1%, namely $3 \times 10 \exp(-4)$. If one were to assume that this fraction of beam energy would be absorbed by a single column of cells, the number of cells in the column would be equal to the cube root of the number of cells in the roughly spherical human brain, $10 \exp(10)$ cells, the cube root being approximately 3,000 cells.

Upon comparison of the absorption of radiation, in the case of the invention with the case of a standard spectrophotometer wherein each unit of material absorbs the same fraction of the beam energy, in the case of the invention, the entire beam energy is absorbed by a single cell in the column of cells. Thus, in order to absorb the same amount of radiation as an ordinary CT scan (and thus in an ordinary skull x-ray), a single cell of the column of cells would have to absorb 1/3000 of the foregoing fraction ($3 \times 10 \exp(-4)$) of the beam energy, this giving a fraction of $10 \exp(-7)$ of the beam energy. During the swept frequency mode of operation, the duty cycle of the modulation, namely the percentage of time which the modulation is at a specific frequency of the stepwise ramp, limits the exposure of tissue to the foregoing fraction of the energy of the beam at each frequency of modulation of the x-ray beam.

Therefore, even though each resonant cell absorbs the entire available beam energy at that frequency, it absorbs no more than it would from an ordinary plain film type of x-ray imaging, yet the cell absorbs 3,000 times as much as the neighboring cells, and 100 times as much as does the bone of the skull. Therefore, the practice of the invention allows safe but effective detection by the CT scanner.

Once the unique frequency of absorption of the modulated x-ray beam has been determined, as noted above, selective destruction of undesirable structures such as oncogenes, viruses, or other macromolecular nucleic acid configurations can be accomplished by scanning the patient a second time. At the second time, the klystron is tuned to the unique resonant frequency of the absorption throughout the duration of the x-ray beam. In this way, the duty cycle during absorption is increased at a factor of approximately $10 \exp(9)$, assuming an interval of $10 \exp(-9)$ seconds for pulse duration including leading and trailing edges of the pulse during the swept frequency mode.

Even if every cell of one of the approximately ten cell types in the brain were malignant, the increased dosage of radiations specific to to the cells, wherein each cell absorbs the radiant energy, would be sufficient to eliminate or deimmortalize all of the cells. In practice, a tumor becomes symptomatic at a cell volume of approximately $10 \exp(5)$ cells, so that the effective dosage delivered to such a tumor would be $10 \exp(4)$ rads per cell. In comparison, the total radiation dose on a CAT scan is on the order of one rad. The foregoing dosage of $10 \exp(4)$ rads per cell is the curative maximum dosage used in radio therapy. There is a significant difference in that in the present case, the dosage delivered to the other nonmalignant cells (which do not absorb significant energy at the resonant frequency of the malignant cells) is still only one additional rad for the second scan. However, the lethal tumor dose of 5,000 rads represents a total, each cell only absorbing $10 \exp(-5)$ of this total, approximately 0.1 rad. In the case of neoplastic cells, a somewhat greater multiple of the same order of magnitude is obtained. With the technique of the invention, the dosage can be multiplied by a factor of $10 \exp(5)$. Even if repair is allowed for, which may underlie the principle of fractionation of the 5,000 rads into 200 rad dosage to minimize radiation damage to other tissues, the net lethal effect on target tissue of the inventive technique is greater than 100 times that of conventional radiotherapy. This is 10,000 times actual dose to target tissue, In contrast, radiation exposure of nontargeted tissue is 3,000 times less than a diagnostic x-ray series. Also, with respect to the foregoing fractionation of the 5,000 rads into 200 rad doses, it is noted that selective absorption of malignant tissue is relatively minimal in conventional radiotherapy compared to the results obtained by the practice of the invention.

With the procedure of the invention, the dose can also be fractioned by reducing the duty cycle if 100 times the lethal tumor dose is not required, depending on the clinical situation, such as the size of the tumor. Higher doses can be achieved also if desired by repeating the scan at full duty cycle, each repetition doubling the dose to the malignancy with negligible additional radiation to healthy tissue. Also, in accordance with the foregoing practice of the invention, once the unique frequency of resonant absorption is determined using the CT scanner, use of the klystron or other modulating device can be accomplished with the x-ray source of the scanner or other conventional x-ray equipment, whether a simple diagnostic x-ray tube or radio therapy equipment, in order to modulate its beam so as to achieve a more rapid treatment session than can be accomplished with a CAT scanner that has not been modified to include the apparatus of the invention.

It should be noted that, unlike other techniques which selectively target tissue in a spatial manner by limiting radiation to a small area at the site of a tumor, the method and apparatus of the invention is highly selective against undesirable tissue, is not limited in space, and can destroy those malignant cells outside the main tumor bulk which are responsible for recurrence, failed surgery, and matastesis. It would appear that the practice of the invention can be used in a total body fashion to cure metastatic malignancy because of the high selectivity and consequent high safety factor and effectiveness.

Furthermore, since the detection process is empirical, determining which frequency is uniquely absorbed by the malignancy, the detection process does not depend on the cause or causes of cancer. As long as there is an abnormal genetic configuration unique to the tumor, even if there be an inactivated or abnormally absent gene, the change in that length of the DNA molecule comprising the chromosome should result in a unique pattern of absorption with consequent destruction of the tumor by the radiation.

With respect to the use of the radiation equipment of the CT scanner, including the klystron as a microwave modulator, both of these devices have established safety and effectiveness. Guidelines for use have been established including shielding requirements. Use of the invention does not change the penetrating characteristics of the x-radiation, so that the operating characteristics would still pertain, in particular with regard to shielding. Both the penetrating characteristics and the amount of shielding are well established. Thus, the invention provides enhanced effectiveness at no cost to safety.

It is to be understood that the above described embodiment of the invention is illustrative only, and that modifications thereof may occur to those skilled in the art. Accordingly, this invention is not to be regarded as limited to the embodiment disclosed herein, but is to be limited only as defined by the appended claims.

What is claimed is:

1. A radio therapy treatment system for radiating a subject comprising:
   means for generating an x-ray beam; and amplitude modulation means operative with said generating means for providing amplitude modulation of the x-ray beam at a predetermined microwave frequency.

2. A system according to claim 1 further comprising selecting means including means operatively coupled to said modulation means for selecting a value of microwave modulation frequency equal to a resonant interactive frequency of material within the subject for absorption of radiant energy from the beam by the material.

3. A system according to claim 2 wherein said selecting means includes means for scanning the frequency of modulation, the system further comprising:
   means for detecting radiation propagating through the subject, the detecting means signaling absorption and presence of radiant energy; and
   means coupled to said detecting means for recording a frequency at which radiant energy is absorbed.

4. A system according to claim 3 wherein said x-ray generating means comprises:
   a target and an electron gun for generating a beam of electrons impinging on said target; and
   a klystron disposed along a path of travel of the electrons for modulating an electric field of said gun, the modulating of the electric field producing a bunching of electrons resulting in amplitude modulation of the x-ray beam.

5. A system according to claim 4 further comprising:
   additional ones of said x-ray generating means, said first-mentioned generating means and said additional generating means constituting a plurality of generating means;
   additional ones of said detecting means, said first-mentioned detecting means and said additional detecting means constituting a plurality of detecting means; and
   wherein said plurality of generating means and said plurality of detecting means are distributed symmetrically about a site of the subject, the system further comprising means for sequentially activating said generating means.

6. A system according to claim 1 wherein said modulation of the x-ray beam provides a train of pulses of x-radiation.

7. A method of radio therapy treatment by radiating a subject with radiant energy at a resonant frequency for interaction with selected material of the subject comprising steps of:
   amplitude modulating an x-ray beam with an amplitude modulating signal at a predetermined microwave frequency;
   directing said beam upon the subject;
   sweeping the modulating microwave frequency;
   detecting radiant energy of said beam after passing of said beam through the subject;
   determining a microwave frequency at which absorption of radiant energy of said beam occurs in the subject;
   amplitude modulating said beam at a microwave frequency at which absorption occurs; and
   radiating the subject with the beam, the beam being modulated at the absorption microwave frequency.

8. A method of radio therapy treatment by selective irradiation of pathological material in situ, comprising the steps of:
   amplitude modulating an x-ray beam with an amplitude modulating signal, the modulating signal being at the microwave frequency of selective absorption of radiant energy by the selected pathological material; and
   irradiating the pathological material with the modulated beam, whereby the selected pathological material absorbs the radiant energy of the beam.

9. The method of claim 8, pathological material consists of malignant cells or part thereof.

10. The method of claim 8, wherein the selected pathological material consists of viruses or part thereof.

11. The method of claim 8, wherein the selected pathological material consists of macromolecules.

12. The method of claim 8, and further comprising the step of positionally directing the beam to a specific region of the pathological material.

13. The method of claim 8, further comprising the steps of:
   modulating the x-ray beam with said modulating signal;
   directing said beam upon the pathological material;
   sweeping the modulating frequency;
   detecting radiant energy of said beam after passing of said beam through the selected pathological material; and
   using the detected frequency to modulate the beam for said irradiating step.

14. The method of claim 13, wherein said modulating signal is within the microwave range of frequencies.

* * * * *